United States Patent

Cotteret et al.

[11] Patent Number: 5,207,798
[45] Date of Patent: May 4, 1993

[54] PROCESS FOR DYEING KERATINOUS FIBRES, AT ACID PH USING 6- OR 7-MONOHYDROXYINDOLES AND THE COMPOSITIONS EMPLOYED

[75] Inventors: Jean Cotteret, Verneuil-sur-Seine; Marie P. Audousset, Levallois-Perret, both of France

[73] Assignee: L'Oreal, Paris, France

[21] Appl. No.: 666,187

[22] Filed: Mar. 7, 1991

[30] Foreign Application Priority Data

Mar. 8, 1990 [FR] France .................. 90 02975

[51] Int. Cl.$^5$ ............................. A61R 7/13
[52] U.S. Cl. .................... 8/408; 8/405; 8/406; 8/414; 8/416; 8/423; 8/424; 424/70; 564/441; 564/442
[58] Field of Search ........... 8/405, 406, 408, 414, 8/416, 423, 424; 424/70; 563/441, 442

[56] References Cited

U.S. PATENT DOCUMENTS

| | | | |
|---|---|---|---|
| 2,934,396 | 4/1960 | Charle et al. | 8/11 |
| 4,013,404 | 3/1977 | Parent et al. | 8/423 |
| 4,804,385 | 2/1989 | Grollier et al. | 8/423 |
| 4,808,190 | 2/1989 | Grollier et al. | 8/423 |
| 4,885,006 | 12/1989 | Grollier et al. | 8/423 |
| 4,888,027 | 12/1989 | Grollier et al. | 8/423 |
| 5,034,015 | 7/1991 | Junino et al. | 8/423 |

FOREIGN PATENT DOCUMENTS

| | | |
|---|---|---|
| 0360638 | 3/1990 | European Pat. Off. |
| 2626771 | 8/1989 | France . |
| 2636235 | 3/1990 | France . |
| 2636236 | 3/1990 | France . |
| 2205329 | 12/1988 | United Kingdom . |
| 2207443 | 2/1989 | United Kingdom . |
| 2211517 | 7/1989 | United Kingdom . |

OTHER PUBLICATIONS

French Search Report of FR 90 02975.

Primary Examiner—Paul Lieberman
Assistant Examiner—William S. Parks
Attorney, Agent, or Firm—Cushman, Darby & Cushman

[57] ABSTRACT

Process for dyeing keratinous fibres, in particular human keratinous fibres such as hair, characterized in that there is applied to these fibres a composition containing, in a suitable dyeing mixture, at least one indole-based coupler, of the formula:

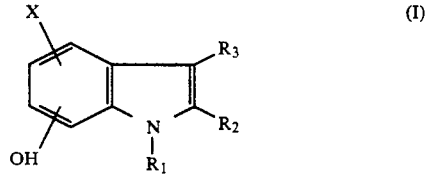

(I)

in which $R_1$ designates a hydrogen atom or a $C_1$–$C_4$ alkyl radical; $R_2$ and $R_3$, which may be identical or different, designate a hydrogen atom, a $C_1$–$C_4$ lower alkyl radical, a carboxyl radical or an alkoxycarbonyl radical; X designates a hydrogen atom, a $C_1$–$C_4$ lower alkyl radical, a $C_1$–$C_{18}$ alkoxy radical, a halogen atom, a $C_2$–$C_{20}$ acyloxy radical or an acetylamino group; the OH group occupying the 6- or 7- positions of the aromatic ring; as well as the salts of these compounds; one oxidation dye precursor; one oxidising agent; the pH of the composition applied to the fibres being less than 7.

20 Claims, No Drawings

PROCESS FOR DYEING KERATINOUS FIBRES, AT ACID PH USING 6- OR 7-MONOHYDROXYINDOLES AND THE COMPOSITIONS EMPLOYED

The present invention relates to a new process for dyeing keratinous fibers, in particular human keratinous fibers, using 5, 6- or 7-hydroxyindoles in combination with oxidation bases and an oxidising agent in acid medium, and to compositions employed during this process.

The dyeing of keratinous fibers, and in particular human hair, using tinctorial compositions containing oxidation dye precursors and in particular p-phenylenediamines or ortho- or para-aminophenols generally called "oxidation bases" and possessing an alkaline pH is known.

It is also known that it is possible to vary the hues obtained with these oxidation bases by combining them with couplers otherwise called color modifiers, chosen in particular from among aromatic meta-diamines, meta-aminophenols and meta-diphenols.

The aim generally is to obtain colorations with good resistance to light, washing, perspiration and to adverse weather conditions, in particular by the choice of couplers and/or oxidation bases which allow such results to be obtained.

The applicants have just discovered that the use of 5-, 6- and/or 7-monohydroxyindole derivatives combined with oxidation bases resulted in colorations possessing an improved tinctorial ability when this combination was applied to hair in the presence of an oxidizing agent at acid pH. The colorations thus obtained possess, moreover, an excellent resistance to light, washing, perspiration and adverse weather conditions.

These results are particularly surprising when they are compared to those obtained with conventional couplers of the benzene series mentioned above where a loss of tinctorial ability and decreased resistance is often observed when the procedure is carried out at acid pH.

The subject of the present invention therefore is a process for dyeing keratinous fibers, in particular human keratinous fibers such as hair, which comprises the application to these fibers of at least one composition containing a 5-, 6- and/or 7-monohydroxyindole derivative, an oxidation dye precursor otherwise called an oxidation base and an oxidizing agent, at acid pH.

Another subject of the invention is a two-component dyeing agent, one of whose components comprises the 5-, 6- or 7-monohydroxyindole derivative and the oxidation dye precursor and the other the oxidizing agent.

Another subject of the invention is the composition which is ready for use, containing the various agents which are used for the dyeing of hair in acid medium.

Other subjects of the invention will emerge from reading the description and the examples which follow.

The process for dyeing keratinous fibers and in particular human keratinous fibers such as hair, in accordance with the invention, is essentially characterized in that there is applied to these fibers at least one composition containing, in a suitable dyeing medium, an indole-based coupler, of the formula:

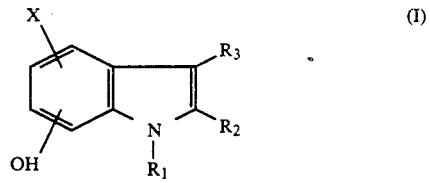

in which $R_1$ designates a hydrogen atom or a $C_1$–$C_4$ alkyl radical; $R_2$ and $R_3$, which may be identical or different, designate a hydrogen atom, a $C_1$–$C_4$ lower alkyl radical, a carboxyl radical or an alkoxycarbonyl radical; X designates a hydrogen atom, a $C_1$–$C_4$ lower alkyl radical, a $C_1$–$C_{18}$ alkoxy radical, a halogen atom, a $C_2$–$C_{20}$ acyloxy radical or an acetylamino group; the OH group occupying the 5- or 6- or 7- positions of the aromatic ring; as well as the salts of these compounds;
at least one oxidation dye precursor or oxidation base;
at least one oxidizing agent; the pH of the composition applied to the fibers being less than 7.

The preferred compounds of the formula (I), used in accordance with the invention, are the compounds in which the alkyl radical preferably designates methyl or ethyl; the alkoxycarbonyl radical designates methoxy or ethoxycarbonyl; the alkoxy radical designates methoxy, ethoxy, butoxy or hexadecyloxy; the acyloxy radical designates acetoxy or tetradecanoyloxy.

Among these compounds, the following may be mentioned: 6-hydroxyindole, 6-hydroxy-3-methoxycarbonylindole, 6-hydroxy-1-methyl-3-methoxycarbonylindole, 6-hydroxy-1-methyl-2,3-dimethoxycarbonylindole, 6-hydroxy-1,2-dimethylindole, 6-hydroxy-2-methylindole, 6-hydroxy-2-carboxyindole, 6-hydroxy-2,3-dimethylindole, 6-hydroxy-3-carboxyindole, 6-hydroxy-3-ethoxycarbonylindole, 6-hydroxy-2-ethoxycarbonylindole, 6-hydroxy-3-methylindole, 6-hydroxy-1-methylindole, 6-hydroxy-5-acetoxyindole, 6-hydroxy-5-methoxyindole, 6-hydroxy-5-methoxy-2-methylindole, 6-hydroxy-5-butoxyindole, 6-hydroxy-5-methoxyindole-2-carboxylic acid, 6-hydroxy-5-methoxy-2,3-dimethylindole, 6-hydroxy-7-methoxyindole, 6-hydroxy-5-tetradecanoyloxyindole, 6-hydroxy-5-hexadecyloxyindole, 7-hydroxyindole, 7-hydroxy-3-methylindole, 7-hydroxy-4-methoxy-2,3-dimethylindole, 6-hydroxy-5-methoxy-1-methylindole, 6-hydroxy-7-methylindole, 6-hydroxy-2-ethoxycarbonyl-5-methoxyindole, 6-hydroxy-2-methoxycarbonyl-5-butylindole, 6-hydroxy-2,3-dimethyl-5-(acetylamino)indole, 5-hydroxy-2-methyl-3-ethoxycarbonylindole and 5-hydroxy-2-carboxyindole.

The salts are chosen more particularly from among the acid addition salts, such as hydrochloric acid, sulphuric acid and the like.

The 5- or 6- or 7-hydroxyindoles which are more particularly preferred are chosen from among 6-hydroxyindole, N-methyl-6-hydroxyindole, 2-carboxy-6-hydroxyindole, N-methyl-5-methoxy-6-hydroxyindole, 7-hydroxyindole, 7-methyl-6-hydroxyindole, 2-methyl-5-methoxy-6-hydroxyindole, 2,3-dimethyl-5-methoxy-6-hydroxyindole, 5-methoxy-6-hydroxyindole, 5-acetoxy-6-hydroxyindole, 7-methoxy-6-hydroxyindole, 2-carboxy-5-methoxy-6-hydroxyindole, 3-methyl-7-hydroxyindole, 5-hydroxyindole, 3-methyl-5-hydroxyindole, 2-ethoxycarbonyl-5-hydroxyindole, 2,3-dimethyl-5-hydroxy-6-methoxyindole and 5-hydroxy-6-methoxyindole.

The oxidation dye precursors or oxidation bases are known compounds in themselves which are not dyes in themselves and which form a dye by a process of oxidative condensation either with themselves or in the presence of a coupler or modifier. These compounds generally contain an aromatic ring bearing functional groups, formed either by two amino groups or by an amino group and a hydroxyl group; these groups being in the para or ortho position with respect to one another.

The para type oxidation dye precursors, used in accordance with the invention, are chosen more particularly from among para-phenylenediamines, para-aminophenols and para-heterocyclic precursors, such as 2,5-diaminopyridine, 2-hydroxy-5-aminopyridine and 2,4,5,6-tetraaminopyrimidine.

Among the para-phenylenediamines, the compounds of the formula (II) may be mentioned more particularly:

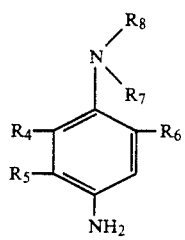

(II)

in which $R_4$, $R_5$ and $R_6$, which may be identical or different, represent a hydrogen or halogen atom, an alkyl radical having from 1 to 4 carbon atoms or an alkoxy radical having from 1 to 4 carbon atoms; $R_7$, and $R_8$, which may be identical or different, represent a hydrogen atom or an alkyl, hydroxyalkyl, alkoxyalkyl, carbamylalkyl, mesylaminoalkyl, acetylaminoalkyl, ureidoalkyl, carbalkoxyaminoalkyl, piperidinoalkyl or morpholinoalkyl radical; these alkyl or alkoxy groups having from 1 to 4 carbon atoms, or $R_7$ and $R_8$, form, together with the nitrogen atom to which they are attached, a piperidino or morpholino heterocycle, on the condition that $R_4$ or $R_6$ represents a hydrogen atom when $R_7$ and $R_8$ do not represent a hydrogen atom, as well as the salts of these compounds.

Among the compounds of the formula (II) which are particularly preferred, the following may be mentioned: p-phenylenediamine, p-toluylenediamine, methoxyparaphenylenediamine, chloro-para-phenylenediamine, 2,6-dimethyl-para-phenylenediamine, 2,5-dimethylparaphenylenediamine, 2,3-dimethyl-para-phenylenediamine, 2-methyl-5-methoxy-para-phenylenediamine, 2,6-dimethyl-5-methoxy-para-phenylenediamine, N,N-dimethyl-paraphenylenediamine, 3-methyl-4-amino-N,N-diethylaniline, N,N-di-(β-hydroxyethyl)-paraphenylenediamine, 3-methyl-4-amino-N,N-di-(β-hydroxyethyl)aniline, 3-chloro-4-amino-N,N-di-(β-hydroxyethyl)aniline, 4-amino-N-ethyl-N-carbamylmethylaniline, 3-methyl-4-amino-N-ethyl-N-carbamylmethylaniline, 4-amino-N-ethyl-N-β-piperidinoethylaniline, 3-methyl-4-amino-N-ethyl-N-β-piperidinoethylaniline, 4-amino-N-ethyl-N-β-morpholinoethylaniline, 3-methyl-4-amino-N-ethyl-N-β-morpholinoethylaniline, 4-amino-N-ethyl-N-β-acetylaminoethylaniline, 4-amino-N-(β-methoxyethyl)aniline, 3-methyl-4-amino-N-ethyl-N-β-acetylaminoethylaniline, 4-amino-N-ethyl-N-β-mesylaminoethylaniline, 3-methyl-4-amino-N-ethyl-N-β-mesylaminoethylaniline, 4-amino-N-ethyl-N-β-sulphoethylaniline, 3-methyl-4-amino-N-ethyl-N-β-sulphoethylaniline, N-[(4'-amino)phenyl]-morpholine and N-[(4'-amino)phenyl]-piperidine.

These para type oxidation dye precursors may be introduced into the tinctorial composition either in the form of a free base or in the form of salts, such as in the form of hydrochloride, hydrobromide or sulphate.

Among the p-aminophenols, the following may be mentioned: p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 2,5-dimethyl-4-aminophenol and 2-methoxymethyl-4-aminophenol.

The ortho type oxidation dye precursors are chosen from among ortho-aminophenols, such as 1-amino-2-hydroxybenzene, 6-methyl-1-hydroxy-2-aminobenzene and 4-methyl-1-amino-2-hydroxybenzene, and ortho-phenylenediamines.

The oxidizing agent is chosen, preferably, from among hydrogen peroxide, urea peroxide, alkaline metal bromates and per salts, such as perborates and persulphates. Hydrogen peroxide is particularly preferred.

The pH of the composition applied to the keratinous fibers, in particular hair, has a value of less than 7 and is preferably between 3 and 6.9. This pH is adjusted using well known acidifying agents in the field of dyeing keratinous fibers, and in particular human hair, such as inorganic or organic acids like hydrochloric acid, tartaric acid, citric acid, phosphoric acid and carboxylic or sulphonic acids.

The compounds of formula (I) of the 5-, 6- or 7-hydroxyindole family are present in the composition applied to the keratinous fibers, preferably in proportions of between 0.01 and 3.5% by weight relative to the total weight of the composition.

The compositions defined above, which are applied in the dyeing of keratinous fibers, may also contain, in addition to the heterocyclic couplers of the 5-, 6- or 7-hydroxyindole family of formula (I), other couplers which are known in themselves, such as meta-diphenols, meta-aminophenols, meta-phenylenediamines, meta-acylaminophenols, meta-ureidophenols, meta-carbalkoxyaminophenols or α-naphthol or couplers containing an active methylene group, such as β-ketonic compounds and pyrazolones.

Among these couplers which may be used in addition to the couplers of the 5-, 6- or 7-dihydroxyindole family of formula (I), the following may be mentioned more particularly: 2,4-dihydroxyphenoxyethanol, 2,4-dihydroxyanisole, meta-aminophenol, resorcinol, resorcinol monomethyl ether, 2-methylresorcinol, 2-methyl-5-N-(β-hydroxyethyl)aminophenol, 2-methyl-5-N-(β-mesylaminoethyl)aminophenol, 6-hydroxybenzomorpholine, 2,4-diaminoanisole, 2,4-diaminophenoxyethanol, 6-aminobenzomorpholine, [2-N-(β-hydroxyethyl)amino-4-amino]phenoxyethanol, 2-amino-4-N-(β-hydroxyethyl)aminoanisole, (2,4-diamino)phenyl-β,γ-dihydroxypropyl ether, 2,4-diaminophenoxyethylamine, 2-methyl-5-aminophenol, 2,6-dimethyl-3-aminophenol, 3,4-methylenedioxyphenol and 3,4-methylenedioxyaniline and their salts.

These compositions may also contain anionic, cationic, non-ionic or amphoteric surface-active agents or their mixtures.

Among these surface-active agents, the following may be mentioned: alkylbenzenesulphonates, alkylnaphthalenesulphonates, the sulphates, ether sulphates and sulphonates of fatty alcohols, quaternary ammonium salts such as trimethylcetylammonium bromide, cetylpyridinium bromide, the ethanolamides of optionally oxyethylenated fatty acids, polyoxyethylenated acids, alcohols or amines, polyglycerolated alcohols, polyoxyethylenated or polyglycerolated alkylphenols, as well as polyoxyethylenated alkylsulphates.

The tinctorial compositions are generally aqueous, but they may also contain organic solvents for solubilizing compounds which may not be sufficiently soluble in water. Among these solvents, the following may be mentioned by way of example: $C_2$–$C_4$ lower alkanols such as ethanol and isopropanol, glycerol, glycols or glycol ethers, such as 2-butoxyethanol, ethylene glycol, propylene glycol, diethylene glycol monoethyl ether and monomethyl ether, as well as aromatic alcohols such as benzyl alcohol or phenoxyethanol, or mixtures of these solvents.

The composition applied to hair may also contain thickening agents chosen in particular from among sodium alginate, gum arabic, cellulose derivatives such as methylcellulose, hydroxyethylcellulose, hydroxypropylcellulose, hydroxymethylcellulose, carboxymethylcellulose, optionally crosslinked acrylic acid polymers and xanthan gum. Inorganic thickening agents such as bentonite may also be used.

The composition may also contain antioxidants chosen in particular from among sodium sulphite, thioglycolic acid, sodium bisulphite, ascorbic acid and hydroquinone, as well as other cosmetically acceptable adjuvants when the composition is intended to be used for dyeing human keratinous fibers, such as penetrating agents, sequestering agents, preservatives, buffers, perfumes and the like.

The compositions used in the process contain neither iodide ion nor nitrite ion in sufficient quantity to oxidize the coupler of formula (I) and the oxidation base.

The composition applied to hair may be presented in various forms, such as liquids, creams, gels or any other suitable form for carrying out capillary dyeing. It may be packaged in aerosol canisters in the presence of a propellant.

Another subject of the invention is the ready-for-use composition which is employed in the process defined above.

According to a particularly preferred embodiment, the process comprises a preliminary stage consisting in storing in a separate form, on the one hand, the composition containing, in a suitable dyeing medium, the indole-based coupler of the formula (I) defined above and the oxidation dye precursors in the form of a component (A) and, on the other, a composition containing the oxidizsing agent such as defined above in the form of a component (B), and carrying out their extemporaneous mixing before applying this mixture to keratinous fibers, as indicated above.

The composition applied to keratinous fibers is obtained in particular from a mixture of 10 to 90% of the component (A) with 90 to 10% of the component (B) containing an oxidizing agent.

Another subject of the invention is an agent for dyeing keratinous fibers, in particular hair, essentially characterized in that it comprises at least two components, one of the components being constituted by the component (A) defined above and the other being constituted by the component (B) also defined above, the pH of the components (A) and (B) being such that after mixing in proportions of 90 to 10% for the component (A) and of 10 to 90% for the component (B), the resulting composition has a pH of less than 7.

In this embodiment, the component (A) which contains at least the indole-based derivative of the 5-, 6- or 7-hydroxyindole family of formula (I) and an oxidation dye precursor may have a pH of between 3 and 10.5 and may be adjusted to the chosen value by means of alkalizing agents normally used in the dyeing of keratinous fibers, such as ammonium hydroxide, alkaline carbonates, alkanolamines such as the mono-, di- and triethanolamines as well as their derivatives or conventional acidifying agents, such as inorganic or organic acids, such as hydrochloric, tartaric, citric and phosphoric acids.

This composition may contain the various other adjuvants mentioned above, particularly couplers other than the couplers of the 5-, 6- or 7-hydroxyindole family of the formula (I) already mentioned above.

All of the oxidation dye precursors of the para and/or ortho type as well as the couplers are preferably present in proportions of between 0.3 and 7% by weight relative to the total weight of the component (A). The concentration of compounds of formula (I) may vary between 0.05 and 4% by weight relative to the total weight of the component A.

The surface-active agents are present in the component (A) in proportions of 0.1 to 55% by weight. The solvent agents optionally present in addition to water are present in proportions of between 0.5 and 40% by weight and in particular between 5 and 30% by weight relative to the total weight of the component (A). The thickening agents are preferably present in proportions of between 0.1 and 5% and in particular between 0.2 and 3% by weight. The antioxidants mentioned above are preferably present in the component (A) in proportions of between 0.02 and 1.5% by weight relative to the total weight of the component (A).

The component (B) which contains the oxidizing agent as defined above has a pH of less than 7. This pH may have a minimum value of 1 and preferably it is between 1.5 and 3.5. This component (B) may be acidified with the same type of acidifying agents as those used for the component (A).

It may be presented in the form of more or less thick liquids, milk or gel.

This two-component dyeing agent may be packaged in a multi-compartment device or dyeing kit, or any other multi-compartment packaging system one of whose compartments contains the component(A) and the second compartment contains the component (B); these devices may be equipped with a means permitting the desired mixture to be delivered to the hair, such as the devices described more particularly in U.S. Pat. No. 4,823,985.

Another subject of the invention is the use, as a coupler, of 6- or 7-hydroxyindole derivatives of the formula (I) for the dyeing in acid medium of keratinous fibers, in combination with oxidation dye precursors.

In accordance with the invention, the dyeing process consists in applying the mixture obtained to the hair, in allowing to settle for 3 to 40 minutes, then in rinsing the hair and optionally carrying out a shampooing.

It is also possible, in accordance with the invention, to apply separately a composition containing the indole-based coupler of formula (I), the oxidation dye precursor and the oxidizing agent, in a manner such that the mixture which forms in situ on the fibers has a pH of less than 7, as defined above.

The following examples are intended to illustrate the invention without, as a result, implying any limitation.

EXAMPLES 1 to 23

The dyeing of hair is carried out by applying to grey hair which is 90% white a mixture of equal weights of the dyeing composition (A) and the oxidizing composition (B), prepared immediately before use.

This mixture has the pH indicated in the table of examples which follow. This mixture is allowed to act for 30 minutes, then the hair is rinsed, and a shampooing is carried out. After drying, the hair is dyed in the hue defined at the bottom of the table herein.

| | 1 | 2 | 3 |
|---|---|---|---|
| A) Dyeing composition (component A) | | | |
| 6-hydroxy-5-acetoxyindole | 0.573 | | |
| 6-hydroxy-N-methylindole | | 0.441 | |
| 6-hydroxy-5-methoxy-2-methylindole | | | 0.708 |
| Para-phenylenediamine | 0.324 | | |
| 2,6-dimethyl-para-phenylenediamine | | 0.657 | |
| 2-methyl-para-phenylenediamine, 2 HCl | | | 0.488 |
| Monoethanolamine qs pH | 9.7 | 8.9 | 9.2 |
| Dye mixture 1 | X | | |
| Dye mixture 2 | | X | X |
| Water qs to | 100 | 100 | 100 |
| B) Oxidizing composition (component B) | | | |
| 20 volumes hydrogen peroxide solution | | | |
| Phosphoric acid qs pH | 1 | 1 | 1 |
| pH mixture w/w A + B | 4.3 | 6.7 | 6.7 |
| Hues obtained | ashen iridescent dark blond | iridescent coppery dark blond | dull ash chestnut |

| | 4 | 5 | 6 |
|---|---|---|---|
| A) Dyeing composition (component) | | | |
| 6-hydroxy-2-carboxyindole | 0.354 | | |
| 6-hydroxy-5-methoxy-2,3-dimethylindole | | 0.573 | |
| 7-hydroxy-3-methylindole | | | 0.294 |
| Para-phenylenediamine | 0.216 | | 0.216 |
| 2,6-dimethyl-para-phenylenediamine | | 0.657 | |
| 3-(β-hydroxyethylamino)-6-methylphenyl | 0.05 | | |
| Meta-aminophenol | 0.05 | | |
| γ-naphthol | 0.05 | | |
| Monoethanolamine qs pH | 9 | 8.9 | 9.2 |
| Dye mixture 2 | X | X | X |
| Water qs to | 100 | 100 | 100 |
| B) Oxidizing composition (component B) | | | |
| 20 volumes hydrogen peroxide solution | | | |
| Phosphoric acid qs pH | 1 | 1 | 1 |
| pH mixture w/w A + B | 6.5 | 6.4 | 6.7 |
| Hues obtained | pearly beige auburn | ash dark blond | beige blond |

| | 7 | 8 | 9 |
|---|---|---|---|
| A) Dyeing composition (component A) | | | |
| 6-hydroxyindole | 0.532 | | |
| 6-hydroxy-7-methoxyindole | | 0.489 | |
| 7-hydroxyindole | | | 0.399 |
| Para-aminophenol | 0.432 | | |
| 2,6-dimethyl-para-phenylenediamine | | 0.657 | |
| Para-phenylenediamine | | | 0.327 |
| Monoethanolamine qs pH | 9.2 | 9.4 | 9.8 |
| Dye mixture 1 | | X | X |
| Dye mixture 2 | X | | |
| Water qs to | 100 | 100 | 100 |
| B) Oxidizing composition (component B) | | | |
| 20 volumes hydrogen peroxide solution | | | |
| Phosphoric acid qs pH | 1 | 1.5 | 1.5 |
| pH mixture w/w A + B | 6.7 | 6.6 | 5 |
| Hues obtained | golden very light blond | blue | chestnut |

| | 10 | 11 |
|---|---|---|
| A) Dyeing composition (component A) | | |
| 6-hydroxyindole | | 0.399 |
| 6-hydroxy-5-methoxy-N-methylindole | 0.531 | |
| 2,6-dimethyl-para-phenylenediamine | 0.657 | 0.657 |
| Monoethanolamine qs pH | 8.9 | 9.8 |
| Dye mixture 1 | | X |
| Dye mixture 2 | X | |
| Water qs to | 100 | 100 |
| B) Oxidizing composition (component B) | | |
| 20 volumes hydrogen peroxide solution | | |
| Phosphoric acid qs pH | 1 | 1.5 |
| pH mixture p/p A + B | 6.3 | 6.5 |
| Hues obtained | iridescent mahogany dark blond | light coppery intense red |

| | 12 | 13 | 14 | 15 |
|---|---|---|---|---|
| A) Dyeing composition (component A) | | | | |
| 6-hydroxyindole | | | | |
| 6-hydroxy-7-methylindole | 0.44 | | | |
| 2-carboxy-5-methoxy-6-hydroxyindole | | 0.62 | | |
| 5-methoxy-6-hydroxyindole | | | 0.49 | |
| 5-acetoxy-6-hydroxyindole | | | | 0.57 |
| 2,3-dimethyl-5-acetylamino-6-hydroxyindole | | | | |
| Para-phenylenediamine | 0.32 | 0.32 | 0.32 | |
| 2,6-dimethyl-para-phenylenediamine, 2 HCl | | | | 0.63 |
| 2-methoxymethyl-para-aminophenol | | | | |
| Monoethanolamine qs pH | 9.2 | 9.2 | 9.2 | 8.7 |
| Dye mixture 3 | X | X | X | X |
| Water qs to | 100 | 100 | 100 | 100 |
| B) Oxidizing composition (component B) | | | | |
| 20 volumes hydrogen peroxide solution | | | | |
| Phosphoric acid qs pH | 1 | 1 | 1 | 1 |
| pH mixture w/w A + B | 6.8 | 6.8 | 6.8 | 6.3 |
| Hues obtained on permanent-waved hair which is 90% white | red mahogany chestnut | ashen iridescent auburn | intense red iridescent | iridescent dark purple |

| | 16 | 17 | 18 |
|---|---|---|---|
| A) Dyeing composition (component A) | | | |
| 6-hydroxyindole | | 0.4 | |
| 6-hydroxy-7-methylindole | | | |
| 2-carboxy-5-methoxy-6-hydroxyindole | | | |
| 5-methoxy-6-hydroxyindole | | | |
| 5-acetoxy-6-hydroxyindole | 0.57 | | |

| | | | |
|---|---|---|---|
| 2,3-dimethyl-5-acetylamino-6-hydroxyindole | | | 0.65 |
| Para-phenylenediamine | | | |
| 2,6-dimethyl-para-phenylene-diamine, 2 HCl | | | 0.63 |
| 2-methoxymethyl-para-aminophenol | 0.46 | 0.46 | |
| Monoethanolamine qs pH | 9.3 | 9.3 | 9.1 |
| Dye mixture 3 | X | X | X |
| Water qs to | 100 | 100 | 100 |
| B) Oxidizing composition (component B) | | | |
| 20 volumes hydrogen peroxide solution | | | |
| Phosphoric acid qs pH | 1 | 1.5 | 1 |
| pH mixture w/w A + B | 6.5 | 6.9 | 6.6 |
| Hues obtained on permanent-waved hair which is 90% white | ash beige light blond | golden ash very light natural blond | ash auburn |

| | 19 | 20 | 21 |
|---|---|---|---|
| A) Dyeing composition (component A) | | | |
| 5-hydroxyindole | 0.399 | | |
| 3-methyl-5-hydroxyindole | | 0.44 | |
| 2-ethoxycarbonyl-5-hydroxyindole | | | 0.615 |
| 2,3-dimethyl-5-hydroxy-6-methoxyindole | | | |
| 5-hydroxy-6-methoxyindole | | | |
| Para-phenylenediamine | 0.324 | | |
| 2,6-dimethyl-para-phenylenediamine, 2 HCl | | | 0.627 |
| Para-aminophenol | | 0.327 | |
| Monoethanolamine qs pH | 9.2 | 9.2 | 9.1 |
| Dye mixture 3 | X | X | X |
| Water qs to | 100 | 100 | 100 |
| B) Oxidizing composition (component B) | | | |
| 20 volumes hydrogen peroxide solution | | | |
| Phosphoric acid qs pH | 1 | 1 | 1 |
| pH mixture w/w A + B | 6.6 | 6.6 | 6.5 |
| Hues obtained on natural hair which is 90% white | dark purple | pearly beige | light dark purple ash |

| | 22 | 23 |
|---|---|---|
| A) Dyeing composition (component A) | | |
| 5-hydroxyindole | | |
| 3-methyl-5-hydroxyindole | | |
| 2-ethoxycarbonyl-5-hydroxyindole | | |
| 2,3-dimethyl-5-hydroxy-6-methoxyindole | | 0.573 |
| 5-hydroxy-6-methoxyindole | 0.489 | |
| Para-phenylenediamine | | |
| 2,6-dimethyl-para-phenylenediamine, 2 HCl | 0.627 | 0.627 |
| Para-aminophenol | | |
| Monoethanolamine qs pH | 9 | 9 |
| Dye mixture 3 | X | X |
| Water qs to | 100 | 100 |
| B) Oxidizing composition (component B) | | |
| 20 volumes hydrogen peroxide solution | | |
| Phosphoric acid qs pH | 1 | 1 |
| pH mixture w/w A + B | 6.7 | 6.6 |
| Hues obtained on natural hair which is 90% white | blue | ashen dull grey |

DYE MIXTURE No. 1

| | |
|---|---|
| Nonylphenol containing 4 moles of ethylene oxide, sold under the name SINNOPAL NP4 by the company HENKEL | 25.5 g |
| Nonylphenol containing 9 moles of ethylene oxide, sold under the name SINNOPAL NP9 by the company HENKEL | 17.5 g |
| Ethylene glycol butyl ether | 7.0 g |
| Propylene glycol | 11.0 g |
| Ethyl alcohol | 2.0 g |
| Monoethanolamine lauryl ether sulphate, sold under the name SACTIPON 2 OM 29 by the company LEVER and containing 28% AS | 5.0 g AS |
| Sodium metabisulphite in aqueous solution containing 35% AS | 0.46 g AS |
| Sodium acetate | 0.8 g |
| Antioxidant, sequestering agent, qs | |

DYE MIXTURE No. 2

| | |
|---|---|
| Polyglycerolated oleic alcohol containing 2 moles of glycerol | 4.0 g |
| Polyglycerolated oleic alcohol containing 4 moles of glycerol, 78% AS | 5.69 g AS |
| Oleic acid | 3.0 g |
| Oleic amine 2 OE sold under the name ETHOMEEN O 12 by the company AKZO | 7.0 g |
| Diethylaminopropyl laurylamino-succinamate, sodium salt containing 55% AS | 3.0 g AS |
| Oleic alcohol | 5.0 g |
| Coconut acid diethanolamide | 12.0 g |
| Propylene glycol | 4.0 g |
| Ethyl alcohol | 7.0 g |
| Propylene glycol monomethyl ether | 9.0 g |
| Sodium bisulphite in aqueous solution containing 35% AS | 0.46 g AS |
| Ammonium acetate | 0.8 g |
| Antioxidant, seqestering agent, qs | |

DYE MIXTURE No. 3

| | |
|---|---|
| Polyglycerolated oleic alcohol containing 2 moles of glycerol | 4.0 g |
| Polyglycerolated oleic alcohol containing 4 moles of glycerol, 78% AS | 5.69 g AS |
| Oleic acid | 3.0 g |
| Oleic amine 2 OE sold under the name ETHOMEEN O 12 by the company AKZO | 7.0 g |
| Diethylaminopropyl laurylamino-succinamate, sodium salt containing 55% AS | 3.0 g AS |
| Oleic alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% AS | 0.46 g AS |
| Ammonium acetate | 0.8 g |
| Antioxidant, sequestering agent, qs | |

We claim:

1. A process for dyeing keratinous fibers consisting of applying to said fibers a composition comprising, in a medium suitable for dyeing said fibers, a combination of
    (a) at least one 5-, 6- or 7- hydroxyindole derivative having the formula

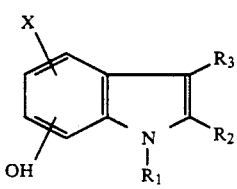

wherein
$R_1$ represents hydrogen or $C_1$–$C_4$ alkyl,

R₂ and R₃, each independently, represent hydrogen, $C_1$–$C_4$ lower alkyl, carboxyl or alkoxy carbonyl, X represents hydrogen, $C_1$–$C_4$ lower alkyl, $C_1$–$C_{18}$ alkoxy, halogen, $C_2$–$C_{20}$ acyloxy or acetylamino, or a salt of the derivative of formula I, said derivative of formula I being present in an amount ranging from 0.01 to 3.5 percent by weight based on the total weight of said composition;

(b) an oxidation dye precursor selected from the group consisting of a paraphenylenediamine, a para-aminophenol, a para-heterocyclie precursor, an ortho-aminophenol and an ortho-phenylenediamine, and (c) an oxidizing agent selected from the group consisting of hydrogen peroxide, urea peroxide, an alkaline metal bromate and a persalt, said oxidation dye precursor (b) and said oxidizing agent (c) being present in an amount effective to dye said keratinous fibers, said composition being free of iodide ions and nitrite ions in an amount sufficient to oxidize said derivative of formula I or said oxidation dye precursor, and said composition when applied to said keratinous fibers having a pH less than 7.

2. The process of claim 1 where in said derivative of formula I, said alkyl represents methyl or ethyl; said alkoxy carbonyl represents methoxycarbonyl or ethoxycarbonyl; said alkoxy represents methoxy, ethoxy, butoxy or hexadecyloxy; and said acyloxy represents acetoxy or tetradecanoyloxy.

3. The process of claim 1 wherein said derivative of formula I is selected from the group consisting of
6-hydroxyindole,
6-hydroxy-3-methoxycarbonylindole,
6-hydroxy-1-methyl-3-methoxycarbonylindole,
6-hydroxy-1-methyl-2,3-dimethoxycarbonylindole,
6-hydroxy-1,2-dimethylindole,
6-hydroxy-2-methylindole,
6-hydroxy-2-carboxyindole,
6-hydroxy-2,3-dimethylindole,
6-hydroxy-3-carboxyindole,
6-hydroxy-3-ethoxycarbonylindole,
6-hydroxy-2-ethoxycarbonylindole,
6-hydroxy-3-methylindole,
6-hydroxy-1-mehtylindole,
6-hydroxy-5-acetoxyindole,
6-hydroxy-5-mehtoxyindole,
6-hydroxy-5-methoxy-2-methylindole,
6-hydroxy-5-butoxyindole,
6-hydroxy-5-methoxyindole-2-carboxylic acid,
6-hydroxy-5-methoxy-2,3-dimethylindole,
6-hydroxy-7-methoxyindole,
6-hydroxy-5-tetradecanoyloxyindole,
6-hydroxy-5-hexadecyloxyindole,
7-hydroxyindole,
7-hydroxy-3-methylindole,
7-hydroxy-4-methoxy-2,3-dimethylindole,
6-hydroxy-5-methoxy-1-methylindole,
6-hydroxy-7-methylindole,
6-hydroxy-2-ethoxycarbonyl-5-methoxyindole,
6-hydroxy-2-methoxycarbonyl-5-butylindole,
6-hydroxy-2,3-dimethyl-5-(acetylamino) indole,
5-hydroxy-2-methyl-3-ethoxycarbonylindole and
5-hydroxy-2-carboxylindole,.

4. The process of claim 1 wherein in said para-phenylenediamine has the formula

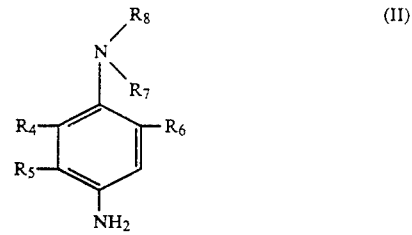

wherein
R₄, R₅ and R₆, each independently, represent hydrogen, halogen, alkyl having 1–4 carbon atoms or alkoxy having 1–4 carbon atoms,
R₇ and R₈, each independently, represent hydrogen, alkyl, hydroxyalkyl, alkoxyalkyl, carbonylalkyl, mesylaminoalkyl, acetylaminoalkyl, ureidoalkyl, carbalkoxyaminoalkyl, piperidinoalkyl or morpholinoalkyl; wherein the alkyl or alkoxy groups have from 1–4 carbon atoms; or R₇ and R₈, together with the nitrogen atom to which they are attached, form a piperidino or morpholino heterocycle, with the proviso that R₄ or R₆ represents hydrogen when R₇ and R₈ do not represent hydrogen; and a salt of said para-phenylenediamine of formula II.

5. The process of claim 4 wherein said para-phenylene diamine of formula II is selected from the group consisting of
p-phenylenediamine,
p-toluylenediamine,
methoxy-para-phenylenediamine,
chloro-para-phenylenediamine,
2,6-dimethyl-para-phenylenediamine,
2,5-dimethyl-para-phenylenediamine,
2,3-dimethyl-para-phenylenediamine,
2-methyl-5-methoxy-para-phenylenediamine,
2,6-dimethyl-5-methoxy-para-phenylenediamine,
N,N-dimethyl-para-phenylenediamine,
3-methyl-4-amino-N,N-diethylaniline,
N,N-di-(β-hydroxyethyl)-para-phenylenediamine,
3-methyl-4-amino-N,N-di-(β-hydroxyethyl) aniline,
3-chloro-4-amino-N,N-di-(β-hydroxyethyl) aniline,
4-amino-N-ethyl-N-carbamylmethylaniline,
3-methyl-4-amino-N-ethyl-N-carbamylmethylaniline,
4-amino-N-ethyl-N-β-piperidinoethylaniline,
3-methyl-4-amino-N-ethyl-N-β-piperidinoethylaniline,
4-amino-N-ethyl-N-β-morpholinoethylaniline,
3-methyl-4-amino-N-ethyl-N-β-morpholinoethylaniline,
4-amino-N-ethyl-N-β-acetylaminoethylaniline,
4-amino-N-(β-methoxyethyl) aniline,
3-methyl-4-amino-N-ethyl-N-β-acetylaminoethylaniline,
4-amino-N-ethyl-N-β-mesylaminoethylaniline,
3-methyl-4-amino-N-ethyl-N-β-mesylaminoethylaniline,
4-amino-N-ethyl-N-β-sulphoethylaniline,
3-methyl-4-amino-N-ethyl-N-β-sulphoethylaniline,
N-morpholine and
N-piperidine, said para-phenylene diamine of formula II being in the form of a free base or a salt.

6. The process of claim 1 wherein said para-aminophenol is selected from the group consisting of p-aminophenol,
2-methyl-4-aminophenol,
3-methyl-4-aminophenol,
2-chloro-4-aminophenol,
3-chloro-4-aminophenol,
2,6-dimethyl-4-aminophenol,
3,5-dimethyl-4-aminophenol,
2,3-dimethyl-4-aminophenol,
2-hydroxy-4-aminophenol,
2-(β-hydroxyethyl)-4-aminophenol,
2-methoxy-4-aminophenol,
3-methoxy-4-aminophenol,
2,5-dimethyl-4-aminophenol and
2-methoxymethyl-4-aminophenol.

7. The process of claim 1 wherein the pH of said composition applied to said keratinous fibers ranges from 3 to 6.9.

8. The process of claim 1 wherein said composition, in addition to said derivative of formula (I) also contains another coupler selected from the group consisting of metadiphenol, a meta-aminophenol, a meta-phenylenediamine, a meta-acylaminophenol, a meta-ureidophenol, a meta-carbalkoxyaminophenol, α-naphthol, a β-ketonic compound and a pyrazolone.

9. The process of claim 8 wherein said another coupler is selected from the group consisting of
2,4-dihydroxyphenoxyethanol,
2,4-dihydroxyanisole,
meta-aminophenol,
resorcinol,
resorcinol monomethyl ether,
2-methyl-resorcinol,
2-methyl-5-N-(β-hydroxyethyl) aminophenol,
2-methyl-5-N-(β-mesylaminoethyl) aminophenol,
6-hydroxy-benzomorpholine,
2,4-diaminoanisole,
2,4-diaminophenoxyethanol,
6-aminobenzomorpholine,
phenoxyethanol,
2-amino-4-N-(β-hydroxyethyl) aminoanisole,
(2,4-diamino) phenyl-β-γ-dihydroxypropylether,
2,4-diaminophenoxyethylamine,
2-methyl-5-aminophenol,
2,6-dimethyl-3-aminophenol,
3,4-methylenedioxyphenol and
3,4-methylenedioxyaniline, or a salt of said another coupler.

10. The process of claim 1 wherein said composition also contains an anionic, nonionic or amphoteric surface active agent or a mixture thereof present in an amount ranging from 0.1 to 55 percent by weight; a thickening agent present in an amount ranging from 0.1 to 5 percent by weight; and an antioxidant present in an amount ranging from 0.02 to 1.5 percent by weight.

11. The process of claim 1 wherein said medium suitable for dyeing said fibers is water, a mixture of water and a solvent selected from the group consisting of a $C_2$-$C_4$ lower alkanol, glycerol, a glycol, a glycol ether, diethylene glycol monoethyl ether, diethylene glycol monomethyl ether, an aromatic alcohol and phenoxyethanol, or a mixture of said solvents.

12. An agent for dyeing keratinous fibers comprising at least two components,
one component (A) consisting of an aqueous composition containing, in a medium suitable for dyeing said fibers, (i) as a coupler at least one 5-, 6- or 7-hydroxyindole derivative having the formula

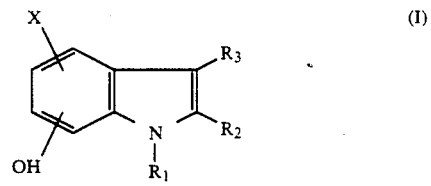

wherein
$R_1$ represents hydrogen or $C_1$-$C_4$ alkyl,
$R_2$ and $R_3$, each independently, represent hydrogen, $C_1$-$C_4$ lower alkyl, carboxyl or alkoxy carbonyl,
X represents hydrogen, $C_1$-$C_4$ lower alkyl, $C_1$-$C_8$ alkoxy, halogen, $C_2$-$C_{20}$ acyloxy or acetylamino, or a salt of the derivative of formula I, said derivative of formula I being present in an amount ranging from 0.05 to 4 percent by weight based on the total weight of said component (A) and
(ii) an oxidation dye precursor selected from the group consisting of a paraphenylenediamine, a para-aminophenol, a para-heterocyclic precursor, an ortho-aminophenol and an ortho-phenylenediamine, said coupler and said oxidation dye precursor being present in an amount ranging from 0.3 to 7 percent by weight based on the total weight of said component (A), and
another component (B) consisting of an aqueous composition containing in a medium suitable for dyeing said fibers an oxidizing agent selected from the group consisting of hydrogen peroxide, urea peroxide, an alkaline metal bromate and a per salt, and present in an amount effective to dye said fibers,
the pH of the mixture of 90 to 10 weight percent of said component (A) and 10 to 90 weight percent of said (B) having a pH less than 7.

13. The agent of claim 12 wherein said component (A) has a pH ranging from 3 to 10.5.

14. The agent of claim 12 where in said component (A) said derivative of formula I is present in an amount ranging from 0.05 to 4 percent by weight based on the total weight of said component (A).

15. The agent of claim 12 wherein said component (A) also contains one or more surface-active agents present in an amount ranging from 0.1 to 55 percent by weight; a solvent, in addition to water, in an amount ranging from 0.5 to 40 percent by weight; a thickening agent in an amount ranging from 0.1 to 5 percent by weight; and an antioxidant in an amount ranging from 0.02 to 1.5 percent by weight.

16. The agent of claim 12 wherein said component B has a pH which has a minimum value of 1 and is less than 7.

17. A process for dyeing keratinous fibers comprising admixing 10 to 90 weight percent of component (A) as defined in claim 12 with 90 to 10 weight percent of component (B) as defined in claim 12 so as to obtain a composition having a pH less than 7 and applying the resulting composition to said keratinous fibers in an amount effective to dye said keratinous fibers.

18. A multi-compartment kit for dyeing keratinous fibers comprising a first compartment containing a component (A) consisting of a composition containing, in a medium suitable for dyeing said fibers, (i) as a coupler at least 5-, 6-, 7-hydroxyindole derivative having the formula

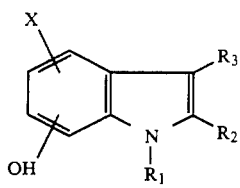
(I)

wherein
R$_1$ represents hydrogen or C$_1$–C$_4$ alkyl,
R$_2$ and R$_3$, each independently, represent hydrogen, C$_1$–C$_4$ lower alkyl, carboxyl or alkoxycarbonyl,
X represents hydrogen, C$_1$–C$_4$ lower alkyl, C$_1$–C$_{18}$ alkoxy, halogen, C$_2$–C$_{20}$ acyloxy or acetylamino, or a salt of the derivative of formula I, said derivative of formula I being present in an amount ranging from 0.05 to 4 percent by weight based on the total weight of said component (A) and (ii) an oxidation dye precursor selected from the group consisting of a paraphenylenediamine, a para-aminophenol, a para-heterocyclic precursor, an ortho-aminophenol and an ortho-phenylenediamine, said coupler and said oxidation dye precursor being present in an amount ranging from 0.3 to 7 weight percent based on the total weight of said component (A), and a second compartment containing a component (B) consisting of a composition containing in a medium suitable for dyeing said fibers an oxidizing agent selected from the group consisting of hydrogen peroxide, urea peroxide, an alkaline metal bromate and a persalt and present in an amount effective to dye said keratinous fibers.

19. The multi-compartment kit of claim 18 equipped with means to deliver a desired mixture of component (A) and component (B) to the said fibers.

20. A ready-for-use composition for dyeing keratinous fibers comprising in a medium suitable for dyeing said fibers a combination of
(a) at least one 5-, 6- or 7-hydroxyindole derivative having the formula

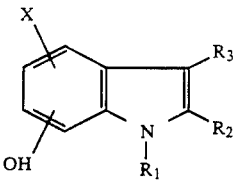
(I)

wherein
R$_1$ represents hydrogen or C$_1$–C$_4$ alkyl,
R$_2$ and R$_3$, each independently, represent hydrogen, C$_1$–C$_4$ lower alkyl, carboxyl or alkoxycarbonyl,
X represents hydrogen, C$_1$–C$_4$ lower alkyl, C$_1$–C$_{18}$ alkoxy, halogen, C$_2$–C$_{20}$ acyloxy or acetylamino, or a salt of the derivative of formula I,
said derivative of formula I being present in an amount ranging from said 0.01 to 3.5 percent by weight based on the total weight of said composition,
(b) an oxidation dye precursor selected from the group consisting of a paraphenylenediamine, a para-aminophenol, a para-heterocyclic precursor, an ortho-aminophenol and an ortho-phenylenediamine, and
(c) an oxidizing agent selected from the group consisting of hydrogen peroxide, urea peroxide, an alkaline metal bromate and a persalt,
said oxidation dye precursor (b) and said oxidizing agent (c) being present in an amount effective to dye said keratinous fibers,
said composition being free of iodide ions and nitrite ions in an amount sufficient to oxidize said derivative of formula I or said oxidation dye precursor,
said composition having a pH less than 7.

* * * * *